(12) United States Patent  (10) Patent No.: US 8,306,653 B2
Chen et al.  (45) Date of Patent: Nov. 6, 2012

(54) UNIFORM TURNOVER MECHANISM AND METHOD FOR CONTROLLING THE SAME

(75) Inventors: Xiaohong Chen, Shenzhen (CN); Shanzhi Huang, Shenzhen (CN); Hua Zhou, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 810 days.

(21) Appl. No.: 12/488,374

(22) Filed: Jun. 19, 2009

(65) Prior Publication Data

US 2010/0082154 A1   Apr. 1, 2010

(30) Foreign Application Priority Data

Sep. 26, 2008  (CN) .......................... 2008 1 0216547

(51) Int. Cl.
 *G06F 7/00* (2006.01)
(52) U.S. Cl. ........................ 700/230; 198/403
(58) Field of Classification Search .................. 700/230; 198/403, 404
 See application file for complete search history.

(56) References Cited

U.S. PATENT DOCUMENTS

| 4,729,533 | A | | 3/1988 | Hillary et al. | |
|---|---|---|---|---|---|
| 6,036,162 | A | * | 3/2000 | Hayashi | 248/550 |
| 6,511,065 | B1 | * | 1/2003 | Cote et al. | 271/270 |
| 6,722,494 | B2 | * | 4/2004 | Nakakado | 198/792 |
| 8,002,104 | B2 | * | 8/2011 | Lim et al. | 198/406 |
| 2002/0125105 | A1 | * | 9/2002 | Nakakado | 198/471.1 |

FOREIGN PATENT DOCUMENTS

| CN | 2109175 | U | 7/1992 |
|---|---|---|---|
| CN | 2342773 | Y | 10/1999 |
| CN | 1617324 | A | 9/2005 |
| CN | 101060810 | A | 10/2007 |
| CN | 101254111 | A | 9/2008 |
| JP | 2006034670 | A | 2/2006 |

\* cited by examiner

*Primary Examiner* — Ramya Burgess
(74) *Attorney, Agent, or Firm* — Kory D. Christensen; Stoel Rives LLP

(57) ABSTRACT

A uniform turnover apparatus comprises a turnover body, a linear advance device, and a fixed base. The linear advance device has a fixed end and a movable end. The fixed end is turnably provided on the fixed base by a first fulcrum. The turnover body is movably connected with the movable end of the linear advance device by a second fulcrum. The turnover body is turnably provided on the fixed base by a third fulcrum. The first, the second, and the third fulcra form a triangle. The uniform turnover apparatus comprises a control device connected with the linear advance device. The control device acquires an actual angular velocity at which the turnover body is turned, and compares the actual angular velocity with a set angular velocity, and according to the comparison, adjusts the linear velocity of the linear advance device in real time, so that the actual angular velocity of the turnover body approximates or equals to the set angular velocity. The apparatus can make the turnover body turn placidly and effectively reduce the impact force during turning over.

10 Claims, 6 Drawing Sheets

UNIFORM TURNOVER MECHANISM AND METHOD FOR CONTROLLING THE SAME

RELATED APPLICATIONS

This application claims priority to Chinese Patent Application No. 200810216547.X, filed Sep. 26, 2008, which is hereby incorporated by reference in its entirety.

TECHNICAL FIELD

The present disclosure relates to a uniform turnover apparatus and a method for controlling the same.

DETAILED DESCRIPTION OF THE DISCLOSURE

Figure 1:
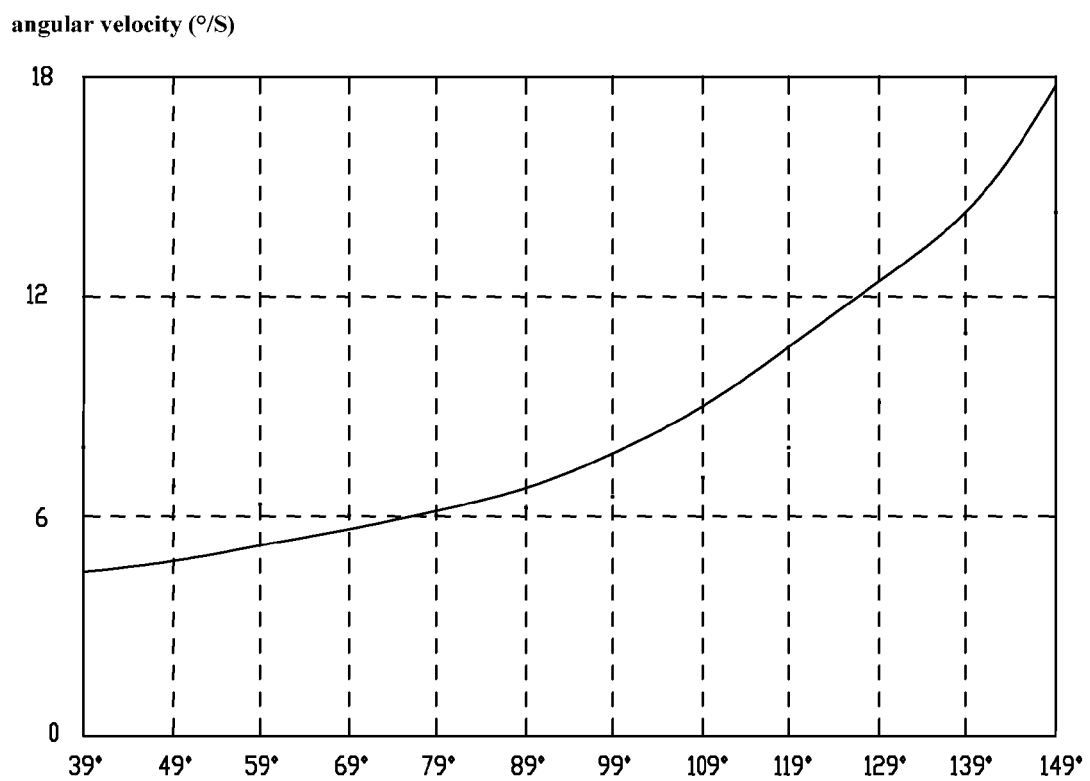
FIG. 1 is a graph showing the functional relationship between angular velocity and angle as a detector is rotated during the conventional electrical tuning (the abscissa is angle and the ordinate is angular velocity)
Figure 2:
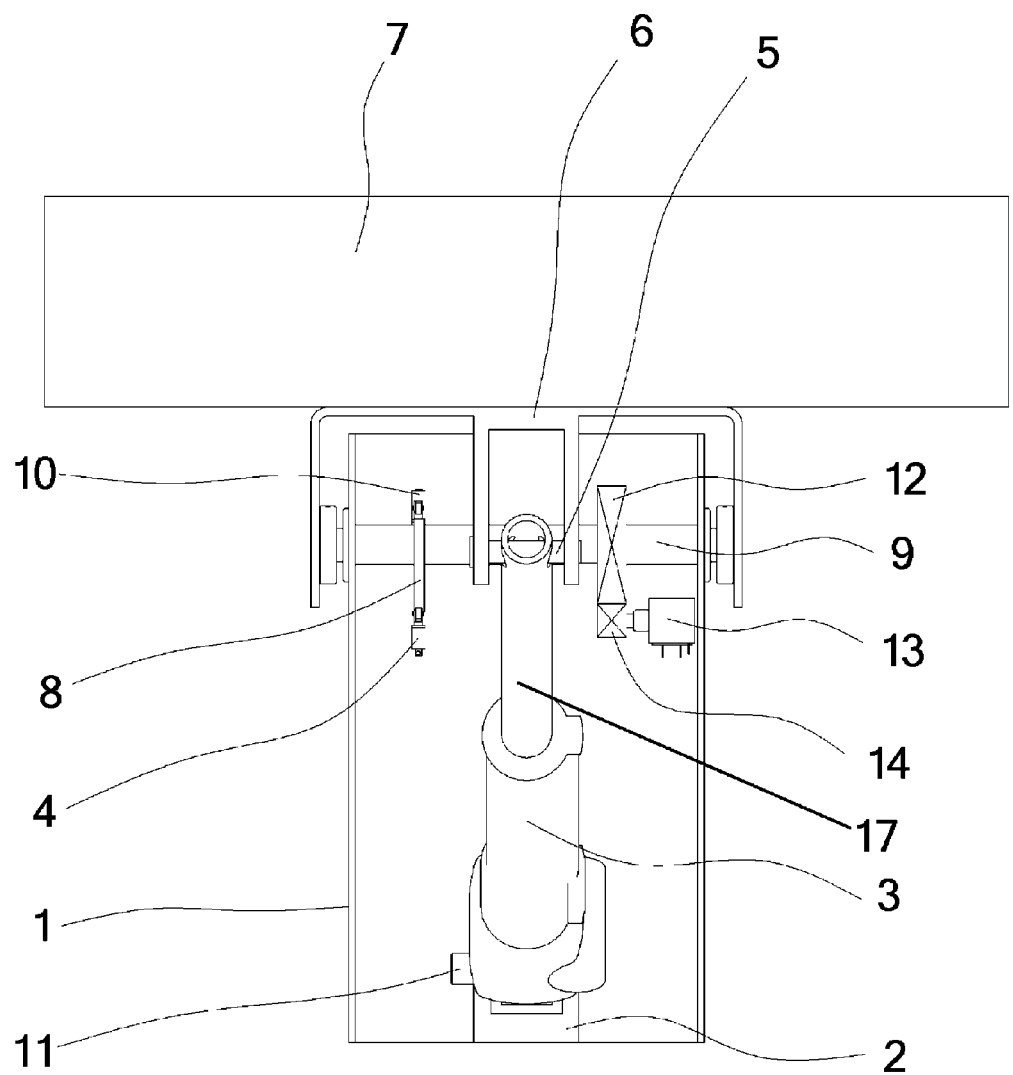
FIG. 2 is a perspective view of a uniform turnover apparatus.
Figure 3:
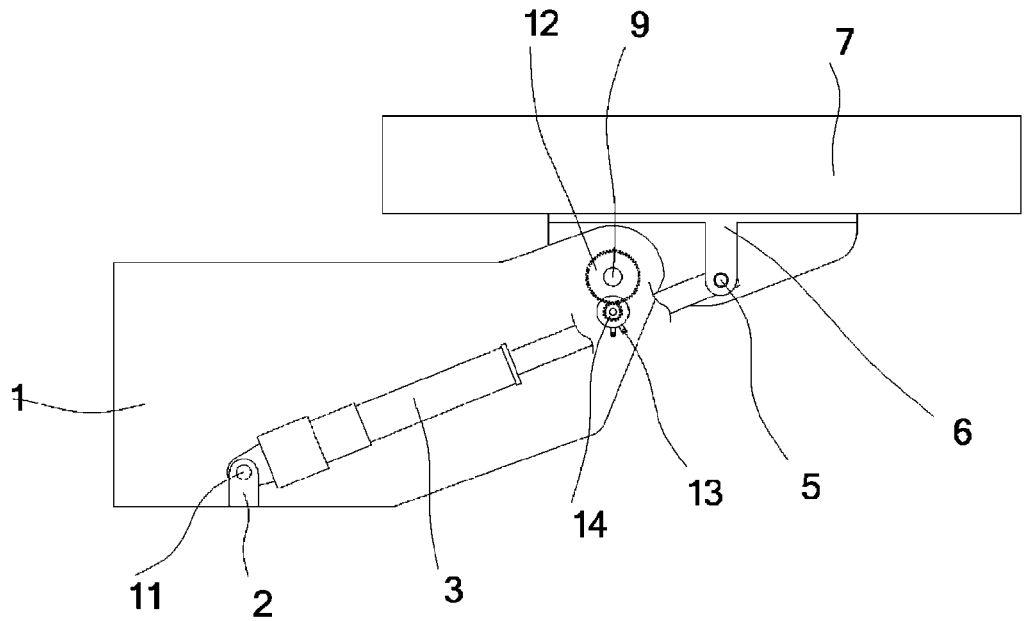
FIG. 3 is a left view of a uniform turnover apparatus.

In a medical X-ray photographic system mounted on a ceiling suspension, a detector of a single-plate system has a plurality of work states, such as an under-table position, where the detector is parallel to a horizontal plane, and a thorax position, where the detector is perpendicular to a horizontal plane. These different work states are achieved by turning over the detector. Currently, a plate turnover is typically achieved by manually or electrically turning over the plate, where the electrical turnover is performed by pushing the detector to move circularly around a shaft by a linear push-rod motor. However, such techniques for turning over the detector have several disadvantages. First, for manually turning over the detector, the doctor cannot use a remote control to control the turning over process and the desired position is therefore hard to achieve in a single operation. Second, for electrically turning over the detector, the angular velocity during the turning over process is not uniform, the process of the turning over is not optimized, and the impact is relatively large during the turning over process, with the ratio of the maximum angular velocity $\omega_{max}$ and the minimum one $\omega_{min}$ of the detector being $\omega_{max}:\omega_{min}\approx 4:1$ as illustrated in FIG. 1.

One aspect of the present disclosure is a uniform turnover apparatus and a method for controlling the same, which can placidly turn the turnover body and effectively reduce the impact force during turning. To achieve this, the uniform turnover apparatus may include a turnover body, a linear advance device, and a fixed base. The linear advance device may have a fixed end and a movable end. The fixed end may be turnably provided on the fixed base by a first fulcrum. The turnover body may be movably connected with the movable end of the linear advance device by a second fulcrum. The turnover body may be turnably provided on the fixed base by a third fulcrum. The first, the second, and the third fulcra may form a triangle.

In one embodiment, the uniform turnover apparatus may further include a control device connected with the linear advance device. The control device may acquire an actual angular velocity at which the turnover body is turned, and compare the actual angular velocity with a set angular velocity, and, according to the comparison, adjust the linear velocity of the linear advance device in real time, such that the actual angular velocity of the turnover body approximates or equals to the set angular velocity.

In one configuration, the third fulcrum is a turnover shaft fixed to the turnover body. A trigger body may be fixed on the turnover shaft. On the fixed base may be fixed a first travel switch and a second travel switch. Both the first travel switch and the second travel switch may be positioned on the turning over trajectory of the trigger body.

The control device may include an angle monitoring device for real-time feedback of an angular position of the turnover body. The trigger body may be a cam, the angle monitoring device may be a potentiometer, and the linear advance device may be a linear push-rod motor.

In one embodiment, the uniform turnover apparatus further includes third turnover shaft. On the third turnover shaft may be fixed a first gear that is engaged with a second gear, where the second gear is synchronously rotated with the potentiometer. The turnover body may include a detector for an X-ray photographic system and a connecting plate fixed thereto. The second and the third fulcra may be connected with the connecting plate.

A method controlling a uniform turnover apparatus may include:
(1) monitoring angular position information of the turnover body and calculating an actual angular velocity of the turnover body according to the angular position;
(2) comparing the actual angular velocity of the turnover body and a set angular velocity;
(3) controlling the linear advance device to reduce linear velocity thereof if the actual angular velocity is larger than the set angular velocity; controlling the linear advance device to increase the linear velocity thereof if the actual angular velocity is smaller than the set angular velocity.

In step (1), the angular position information of the turnover body is monitored in real time by a potentiometer. The linear advance device may be a linear push-rod motor. In step (3), the linear velocity of the linear push-rod motor may be changed by adjusting the duty ratio of driving signal of the linear push-rod motor.

As illustrated in FIGS. 2 to 7, a uniform turnover apparatus according to an embodiment of the disclosure may include a holder 1, a motor base 2, a linear push-rod motor 3, a connecting plate 6, a detector 7, and a potentiometer 13. In one embodiment, the holder 1 is fixed. The motor base 2 may be fixed on the holder 1. The linear push-rod motor 3, which is used to convert rotational movement into linear movement, may have a fixed end and a movable end. The fixed end may be turnably mounted on the motor base 2 by a first turnover shaft 11, such that the linear push-pod motor 3 as a whole can be turned over with respect to the motor base 2 with the first turnover shaft 11 as a fulcrum. The movable end of the linear push-rod motor 3 may be rotatably connected with the connecting plate 6 by a second turnover shaft 5. The connecting plate 6 may be fixed to a third turnover shaft 9 by fasteners.

The third turnover shaft 9 may be connected with the holder 1 by a bearing, such that the third turnover shaft 9 is rotatable on the holder 1.

The detector 7 may be fixed on the connecting plate 6 by fasteners so as to synchronously turnover with the connecting plate 6. The first turnover shaft 11, the second turnover shaft 5, and the third turnover shaft 9 may be arranged in form of triangle and may be parallel to each other. A cam 8 may be fixed on the third turnover shaft 9. A first travel switch 4 and a second travel switch 10 may be fixed on the holder 1. The cam 8 may be rotated between the first and the second travel switches 4 and 10, and may perform the trigger of the first and the second travel switches 4 and 10, respectively. On the third turnover shaft 9 may be further fixed a first gear 12, which is coaxial with the third turnover shaft 9. The first gear 12 is engaged with a second gear 14. The second gear 14 may be fixed on a corresponding gear shaft on which the potentiometer 13 is fixed so that the second gear 14 drives the potentiometer 13 to rotate synchronously. On the third turnover shaft 9, the cam 8 and the first gear 12 may be positioned on the right and left sides of the movable end of the linear push-rod motor 3, respectively.

Figure 4:
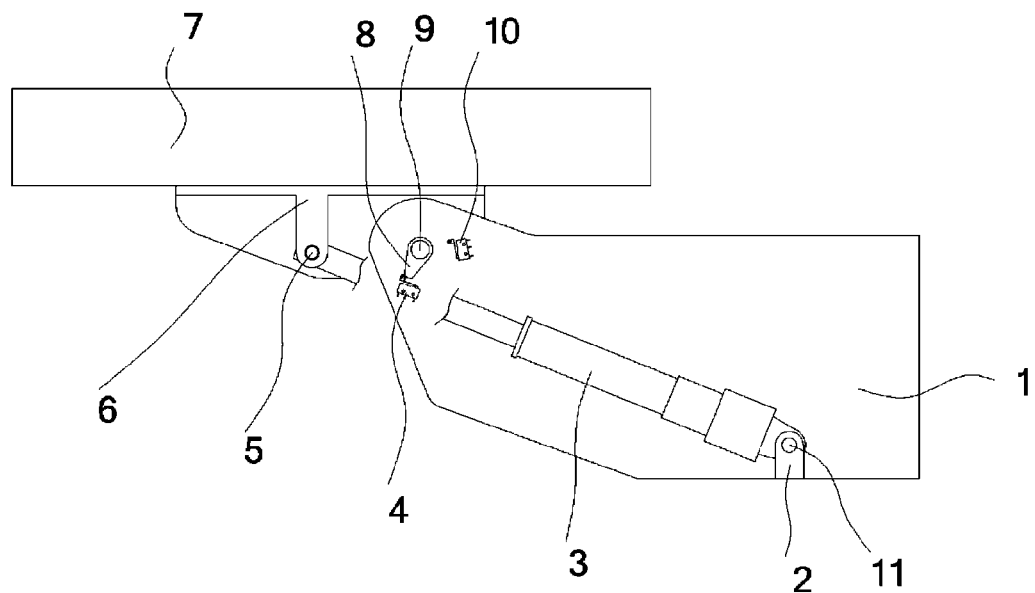
FIG. 4 is a schematic view of a uniform turnover apparatus when the turnover body is in a first limit position.
Figure 5:
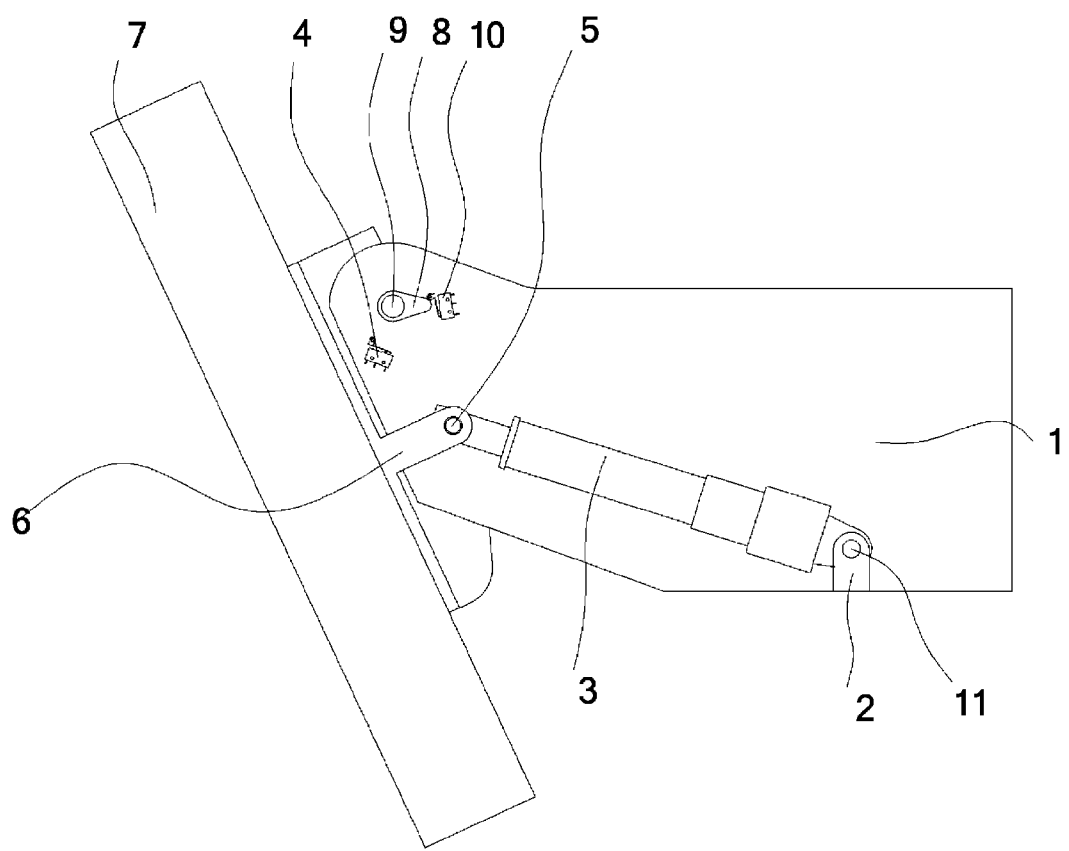
FIG. 5 is a schematic view of a uniform turnover apparatus when the turnover body is in a second limit position.

In one embodiment, the detector 7, the connecting plate 6, the third turnover shaft 9, the cam 8 and the first gear 12 are rotated synchronously, and such a rotation is transferred to the potentiometer 13 by the engaged first gear 12 and second gear 14 at a certain multiple (i.e., a transmission ratio of the gear train consisting of the first and the second gears). When the linear push-rod motor 3 operates, the movable end thereof drives the connecting plate 6 and the detector 7 to turnover with the third turnover shaft 9 as a fulcrum. The limit positions of such a turnover may be determined by the first travel switch 4 and the second travel switch 10. When the detector 7 is on the first limit position, the cam 8 may trigger the first travel switch 4 as illustrated in FIG. 4; and when the detector 7 is on the second limit position, the cam 8 may trigger the second travel switch 10 as illustrated in FIG. 5.

Figure 6:
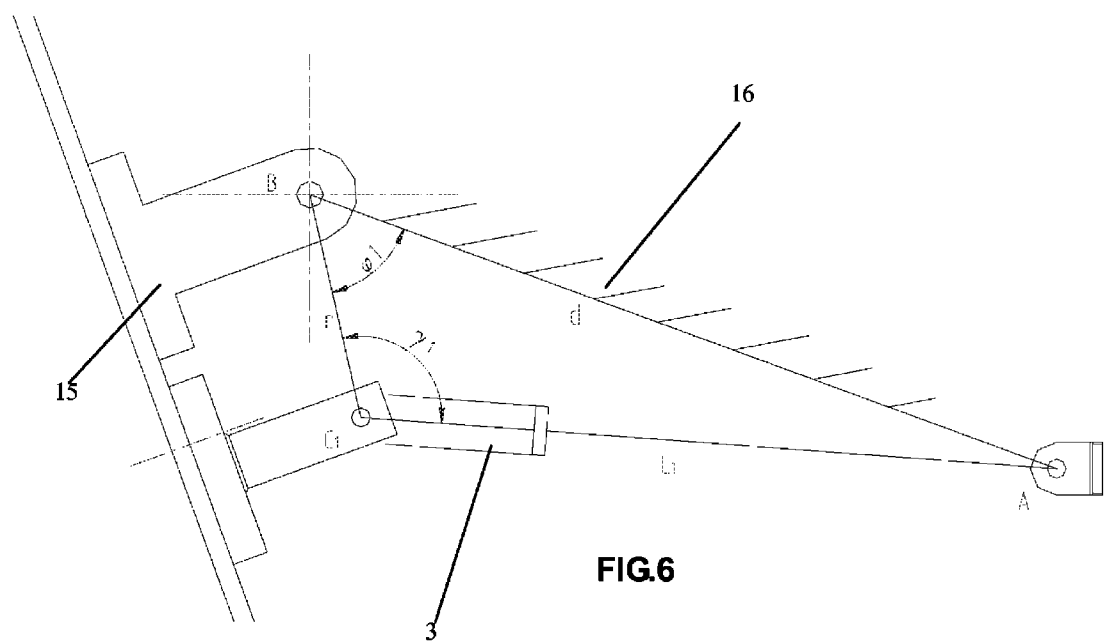
FIG. 6 is a structural schematic diagram of a uniform turnover apparatus.
Figure 7:
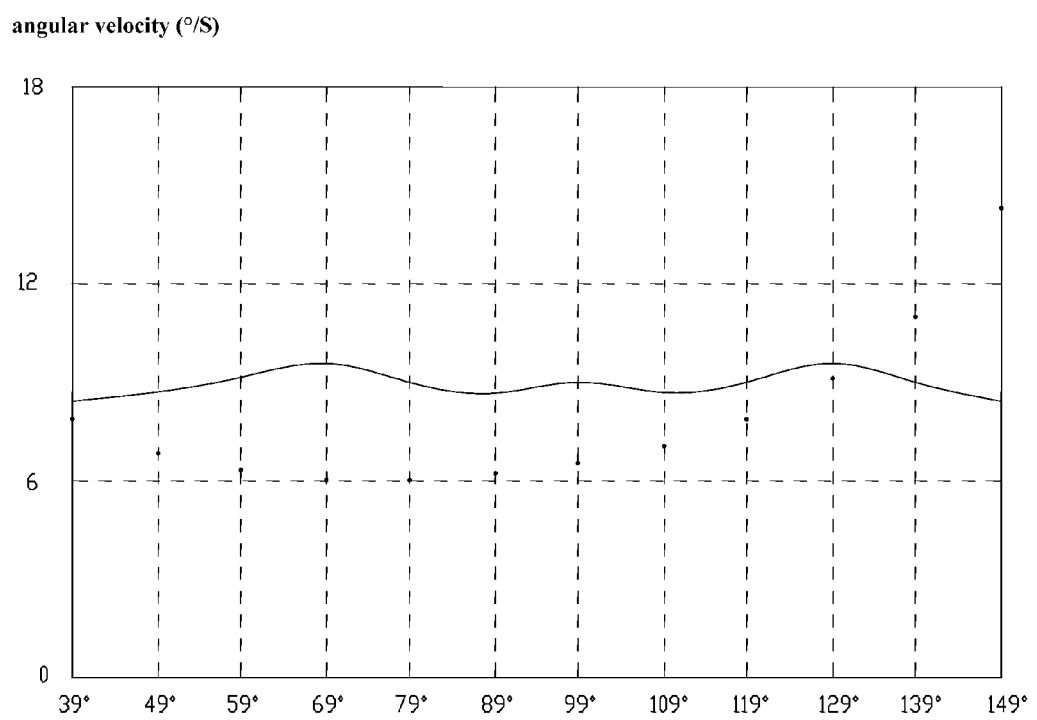
FIG. 7 is a graph showing the functional relationship between angular velocity and angle as the detector of a uniform turnover apparatus is turned (the abscissa is angle and the ordinate is angular velocity).

Referring to FIG. 6, the detector and the connecting plate fixed together may be considered as a whole as a turnover body 15, the holder and the motor base may be considered as a whole as a fixed base 16, and the first, the second, and the third turnover shafts may be considered as the first, the second, and the third fulcra A, C1, and B, respectively. The fixed end of the linear push-rod motor 3 may be turnably mounted on the fixed base 16 by the first fulcrum A. In one embodiment, the movable end of the linear push-rod motor 3 is rotatably connected with the turnover body 15 by the second fulcrum C1. The turnover body 15 may be rotatably mounted on the fixed base 16 by the third fulcrum B. The first, the second, and the third fulcra A, C1, and B may form a triangle AC1B in which the length of side AC1 is L1, the length of side C1B is r, the length of side BA is d and the transmission angle is $\gamma i$.

Supposing $\sigma = r/d$, then:

$$\sin\gamma i = \frac{1}{\sqrt{\left(\frac{\sigma - \cos\varphi i}{\sin\varphi i}\right)^2 + 1}} \qquad (1)$$

When the turnover body 15 is turned over about the third fulcrum B, the angular velocity $\omega_1$ of the turnover body 15 is:

$$\omega_1 = V_2/r\sin\gamma i = \sqrt{\left(\frac{\sigma - \cos\varphi i}{\sin\varphi i}\right)^2 + 1} \cdot V_2/r \qquad (2)$$

Where, $V_2$ is the linear velocity at which the linear push-rod motor 3 operates, i.e., the velocity at which the retractable rod 17 of the linear push-rod motor 3 linearly protrudes or retracts.

From the equation (2) for calculating the angular velocity, if the linear push-rod motor is of uniform movement, i.e., with $V_2$ being constant, the angular velocity of the turnover body is non-uniform (see FIG. 1), while if it is required to make the turnover body turnover at a uniform velocity, the linear push-rod motor is required to have a non-uniform velocity in one embodiment.

In one embodiment, when the linear push-rod motor 3 drives the detector 7 to turn over, the potentiometer 13 feeds back the position information of the detector 7 based on which the actual angle of the detector 7 can be determined. By continuously reading the position information from the detector 7 periodically, the rotated angle of the detector 7 in unit time, i.e., the actual angular velocity of the detector 7 can be determined. The actual angular velocity and a set angular velocity are compared. If they are not equal, the linear velocity of the linear push-rod motor 3 may be adjusted by adjusting the duty ratio of the driving signal of the motor. If the set angular velocity is larger than the actual angular velocity, the duty ratio of the driving signal of the motor may be increased to accelerate the motor, i.e., increase the linear velocity $V_2$; if the set angular velocity is smaller than the actual angular velocity, the duty ratio of the driving signal of the motor may be reduced to decelerate the motor, i.e., reduce the linear velocity $V_2$, whereby the actual angular velocity of the detector approximates or equals to the set angular velocity. As illustrated in FIG. 6, the ratio of the maximum angular velocity $\omega$max and the minimum angular velocity $\omega$min of the detector 7 is $\omega$max: $\omega$min≈1.2:1. Adjusting the linear velocity V2 of the linear push-rod motor 3 is performed according to the foresaid equation for calculating angular velocity $\omega1$.

According to one embodiment, the uniform turnover apparatus includes a turnover body, a linear advance device, a fixed base, and a control device. The linear advance device may have a fixed end and a movable end. The fixed end may be turnably provided on the fixed base by a first fulcrum. The turnover body may be movably connected with the movable end of the linear advance device by a second fulcrum. The turnover body may be turnably provided on the fixed base by a third fulcrum. The first, the second, and the third fulcra may form a triangle.

In one embodiment, the control device is connected with the linear advance device. The control device acquires an actual angular velocity at which the turnover body is turned over, and compares the actual angular velocity with a set angular velocity, and according to the comparison, adjusts the linear velocity of the linear advance device in real time, such that the actual angular velocity of the turnover body approximates or equals to the set angular velocity. By controlling the linear advance device to move non-uniformly, the turnover body can turnover at a uniform velocity or at an approximately uniform velocity, such that the process of the turning over of the turnover body is more stable and the impact force during the turning over movement is reduced.

The uniform turnover apparatus according to the disclosure may further include a position limiting device for positionally limiting the range of the turning over angle of the turnover body. The position limiting device may include a trigger body moved synchronously with the turnover body, and a first travel switch and a second travel switch fixed on the fixed base. Both the first travel switch and the second travel switch may be positioned on the turning over trajectory of the trigger body. The trigger body may be a cam, and alternatively a swing link, or any other structure body serving the function of trigger the travel switches. Preferably, the trigger body is a cam which does not only have a simple structure and light weight, but also can be easily mounted. The travel switch may be a mechanical trigger switch and alternatively a photoelectric trigger switch.

The uniform turnover apparatus according to the disclosure may comprise an angle monitoring device for real-timely feeding back the angular position of the turnover body. The angle monitoring device may be a potentiometer and alternatively any other electronics device serving the same function. The angle monitoring device may be turned over synchronously with the turnover body. Alternatively, the turning over movement of the turnover body may be transferred to the angle monitoring device at a certain transmission ratio. In the case where the angle monitoring device is a potentiometer, the turnover body is turnably provided on the fixed base with a turnover shaft as a fulcrum. On the turnover shaft is fixed a first gear which is engaged with a second gear moved synchronously with the potentiometer. By providing such gear transmission, not only is the structure simple, but also the rotated angle of the turnover shaft can be effectively transferred. Alternatively, the gear transmission may be replaced with synchronous pulley transmission.

The uniform turnover apparatus according to the disclosure may be applied not only in an X-ray photographic system, but also in other systems requiring turning at a uniform velocity.

The above describes the disclosure in detail in conjunction with specific embodiments, but the disclosure should not be considered to be limited to the embodiments. It will be apparent to those skilled in the art that various modifications and changes may be made without departing from the disclosure and should be considered to fall into the scope of the disclosure.

What is claimed is:

1. A uniform turnover apparatus comprising a turnover body, a linear advance device, and a fixed base, the linear advance device having a fixed end and a movable end, the fixed end being turnably provided on the fixed base by a first fulcrum, the turnover body being movably connected with the movable end of the linear advance device by a second fulcrum, the turnover body being turnably provided on the fixed base by a third fulcrum, the first, the second, and the third fulcra forming a triangle, wherein the uniform turnover apparatus further comprises a control device which is connected with the linear advance device, the control device acquiring an actual angular velocity at which the turnover body is turned and comparing the actual angular velocity with a set angular velocity, and according to the comparison, adjusting in real time the linear velocity of the linear advance device, such that the actual angular velocity of the turnover body approximates or equals to the set angular velocity.

2. The uniform turnover apparatus of claim 1, wherein said third fulcrum is a turnover shaft which is fixed to the turnover body, a trigger body being further fixed on the turnover shaft, a first travel switch and a second travel switch being fixed on the first base, both the first travel switch and the second travel switch being positioned on the turning over trajectory of the trigger body.

3. The uniform turnover apparatus of claim 2, wherein said control device comprises an angle monitoring device for providing real time feedback of an angular position of the turnover body.

4. The uniform turnover apparatus of claim 3, wherein said trigger body is a cam, the angle monitoring device is a potentiometer, and the linear advance device is a linear push-rod motor.

5. The uniform turnover apparatus of claim 4, further comprising a third turnover shaft, on which is further fixed a first gear which is engaged with a second gear, wherein said second gear is synchronously rotated with the potentiometer.

6. The uniform turnover apparatus of claim 1, wherein said turnover body comprises a detector for an X-ray photographic system and a connecting plate fixed thereto, the second and the third fulcra being connected with the connecting plate.

7. A method for controlling a uniform turnover apparatus comprising a turnover body, a linear advance device, and a fixed base, the linear advance device having a fixed end and a movable end, the fixed end being turnably provided on the fixed base by a first fulcrum, the turnover body being movably connected with the movable end of the linear advance device by a second fulcrum, the turnover body being turnably provided on the fixed base by a third fulcrum, the first, the second, and the third fulcra forming a triangle, the method comprising the steps of:
(1) monitoring angular position information of the turnover body and calculating an actual angular velocity of the turnover body according to the angular position;
(2) comparing the actual angular velocity of the turnover body and a set angular velocity;
(3) controlling the linear advance device to reduce linear velocity thereof if the actual angular velocity is larger than the set angular velocity; controlling the linear advance device to increase the linear velocity thereof if the actual angular velocity is smaller than the set angular velocity.

8. The method for controlling a uniform turnover apparatus of claim 7, wherein, in step (1), the angular position information of the turnover body is monitored by a potentiometer in real time.

9. The method for controlling a uniform turnover apparatus of claim 7, wherein said linear advance device is a linear push-rod motor.

10. The method controlling a uniform turnover apparatus of claim 9, wherein in step (3), the linear velocity of the linear push-rod motor is changed by adjusting the duty ratio of the driving signal of the linear push-rod motor.

* * * * *